United States Patent
Rao et al.

(10) Patent No.: US 7,923,005 B2
(45) Date of Patent: Apr. 12, 2011

(54) **PROCESS FOR PRODUCING A BIO-PESTICIDE COMPOSITION CONTAINING *TRICHODERMA HARZIANUM* AND *PSEUDOMONAS FLUORESCENS***

(75) Inventors: Mahendrakar Sreenivasa Rao, Hessargatta Lake (IN); Nanjundagowda Ramachandran, Hessarghatta Lake (IN)

(73) Assignees: Department of Biotechnology (IN); Indian Institute of Horticultural Research (IN)

( * ) Notice: Subject to any disclaimer, the term of this patent is extended or adjusted under 35 U.S.C. 154(b) by 217 days.

(21) Appl. No.: 12/088,039

(22) PCT Filed: Feb. 15, 2007

(86) PCT No.: PCT/IN2007/000064
§ 371 (c)(1),
(2), (4) Date: Jul. 23, 2008

(87) PCT Pub. No.: WO2007/094014
PCT Pub. Date: Aug. 23, 2007

(65) Prior Publication Data
US 2008/0286853 A1      Nov. 20, 2008

(30) Foreign Application Priority Data
Feb. 16, 2006    (IN) .............................. 434/DEL/2006

(51) Int. Cl.
*A01N 63/00* (2006.01)
*A01N 63/04* (2006.01)

(52) U.S. Cl. .................... 424/93.3; 424/93.47; 504/117; 435/876; 435/945

(58) Field of Classification Search .................. None
See application file for complete search history.

(56) References Cited

U.S. PATENT DOCUMENTS
2004/0261578 A1    12/2004    Harman et al.

FOREIGN PATENT DOCUMENTS
JP    4160084 A    6/1992

OTHER PUBLICATIONS

Khan et al. Phytopathologia Mediterranea, Aug. 2005, vol. 44, No. 2, pp. 208-215.*
Padmodaya et al. Journal of Mycology and Plant Pathology, Apr. 1999, vol. 29, No. 1, pp. 38-41.*
Sharma et al. Indian Journal of Biotechnology, Jul. 2005, vol. 4, No. 3, pp. 419-421.*
Saravanan et al. Crop Protection, 2003, 22, pp. 1117-1123.*
Baby et al. Tropical Agriculture, 1993, vol. 70, No. 13, pp. 240-244.*

* cited by examiner

*Primary Examiner* — Vera Afremova
(74) *Attorney, Agent, or Firm* — The Webb Law Firm

(57) ABSTRACT

A process for the production of organic and combination formulation of bio-pesticide containing *Trichoderma harzianum* and *Pseudomonas fluorescens* comprising preparation of mother culture, liquid fermentation as well as solid fermentation of *T. harzianum*, preparation of mother culture, liquid fermentation as well as solid fermentation of *P. fluorescens* separately, followed by mixing both the bio-pesticides in the proportion of 1-2: 1-2: preferably 1:1 to get the final combination, formulation.

13 Claims, 1 Drawing Sheet

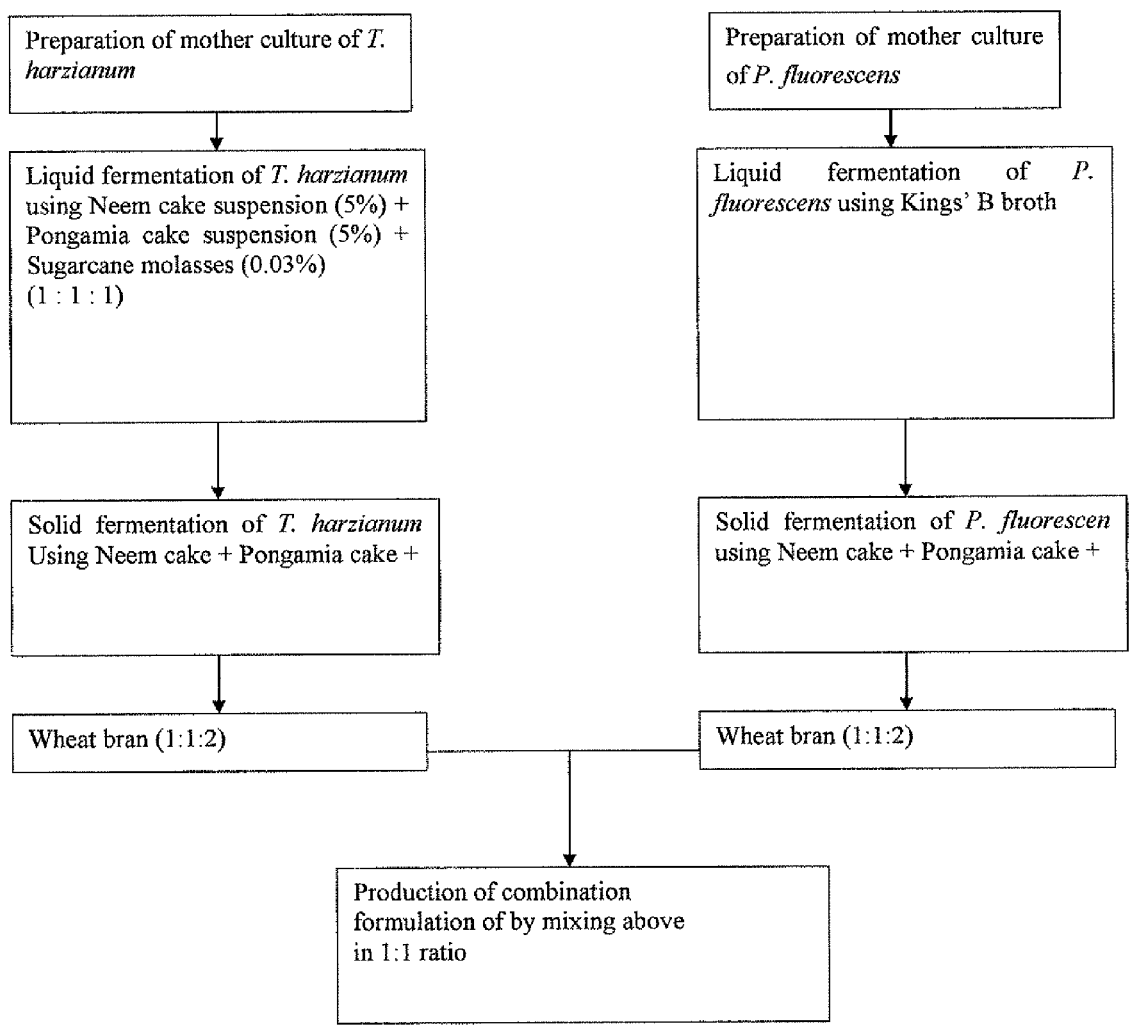

PROCESS FOR PRODUCING A BIO-PESTICIDE COMPOSITION CONTAINING *TRICHODERMA HARZIANUM* AND *PSEUDOMONAS FLUORESCENS*

BACKGROUND OF THE INVENTION

1. Field of Invention

This invention relates to a process for producing a bio-pesticide composition containing *Trichoderma harzianum* and *Pseudomonas fluorescens*.

2. Description of Related Art

A standardized process for mass production of *Trichoderma harzianum* Rifai and *Pseudomonas fluorescens* (Migula) separately is known in the art. Such a process included liquid fermentation step and not solid fermentation. As it is, liquid fermentation process alone would result in the end product of bio-control agent formulation of inferior quality. Hence, by this process it is not economical to produce a bio-pesticide of *T. harzianum* or *P. fluorescens*.

For the management of various soil borne pathogens, formulation of *T. harzianum* is being used widely on the various agricultural crops. Similarly formulation of *P. fluorescens* is also widely used for the management of various soil borne pathogens infecting various agricultural crops. There are also several reports on the efficacy of these two potential bio-agents against various soil borne pathogens infecting various agricultural crops. However, there is no organic product of combination formulation of these two bio-agents.

SUMMARY OF THE INVENTION

An object of this invention is to propose a process for liquid and solid fermentation of *Trichoderma harzianum* using organic materials.

Another object of the present invention is to propose a process for liquid solid fermentation of *Pseudomonas fluorescens* using organic material.

Still another object of the present invention is to propose a preparation containing *T. harzianum* and *P. fluorescens* with an organic carrier.

Yet another object of this invention is to propose a preparation containing *T. harzianum* and *P. fluorescens* which is highly effective for the management of various soil borne pathogens on agricultural crops.

At the outset of the description that follows, it is to be understood that the ensuing description only illustrates a particular form of this invention. However, such a particular form is only an exemplary embodiment and is not intended to be taken restrictively to imply any limitation on the scope of the present invention.

BRIEF DESCRIPTION OF THE DRAWING

The FIGURE is a flowchart describing the production of the combination formulation of *P. fluorescens* and *T. harzianum*.

DESCRIPTION OF THE PREFERRED EMBODIMENT

The process of mass production of combination formulation of *T. harzianum* and *P. fluorescens* include (a) liquid as well as solid fermentation of *T. harzianum* (b) liquid as well as solid fermentation of *P. fluorescens* separately.

1. Fermentation of *Trichoderma harzianum*:

Preparation of Mother Culture:

The isolate is sub cultured on potato dextrose agar medium, which is incubated under dark condition. The discs are cut and inoculate into a conical flask containing Potato Dextrose Broth (PDB) (Hi-medical), and incubated, which can be used for the liquid fermentation.

Liquid Fermentation for the Production of *Trichoderma harzianum*

In the liquid fermentation process, organic materials (4-8%, preferably 5% neem (*Azadirachta indica*) cake suspension+4-8%, preferably 5% pongamia cake extract (*Pongamia pinnata*)+0.02-0.05%, preferably 0.03% sugar cane molasses in the ratio of 1:1:1) are used as substrate. The substrate is autoclaved at 121° C. (15 PSI) for 20 min. for its use in the liquid fermentation process. This is unique feature in this process.

The liquid concentration of neem and pongamia aqueous extracts are prepared by pre-soaking the oil cakes and later decanted and filtered using muslin cloth.

The required concentration of sugar cane molasses (organic material) is prepared by dissolving the molasses (v/v) in a known amount of tap water. All the ingredients are mixed and used as the substrate in the liquid fermentation process. Such as substrate is sterilized in the fermenter. After it is cooled, it is added with the mother culture of the bio-agent prepared using Potato Dextrose Broth (PDB) (Hi-media) (the preparation of the mother culture is mentioned above). The fungal mat is harvested in the aseptic conditions and it is used for the solid fermentation.

Solid Fermentation for the Production of *Trichoderma harzianum*

Solid fermentation is an important step and contributes tremendously for the mass production process making it more efficient and economical. In this stage, organic materials [(neem cake (de oiled cake)+pongamia cake (de oiled cake)+wheat bran in the ratio of 1-3:1-3:1-2, preferably 1:1:2] are used as substrate in the solid fermentation of *Trichoderma harzianum*. The substrate is autoclaved at 121° C. (15 PSI) for 20 min. for use in the solid fermentation process.

The fungal mat obtained through the liquid fermentation is mixed and filled in a tray with the lid and should be left for 7 days for the solid fermentation.

The solid substrate enables the bio-control fungus to produce the maximum number of spores per gram of substrate.

Liquid Fermentation *Pseudomonas fluorescens*:

Preparation of Mother Culture of *P. fluorescens*

The isolate has to be sub cultured on King's B—medium. It should be incubated for 24-36 hours 30±1° C. Later with the help of cork borer (7 mm) the discs should be cut and inoculate into the 500 ml conical flask containing 250 ml of King's B broth. The has to be incubated at 30±1° C. for 24-36 hours and this can be used in the liquid fermentation process.

Liquid Fermentation of *Pseudomonas fluorescens*:

Liquid fermentation of *P. fluorescens* is carried out using a fermenter. Initially, the medium be used will be required quantity of King's B broth. The medium is sterilized and culture of *P. fluorescens* is inoculated to the sterilized broth. Afterwards the liquid fermentation is allowed. Later on this harvested under aseptic conditions and used for solid fermentation.

Composition of King's B medium

| SI. NO. | CHEMICALS | FOR 1000 ML |
| --- | --- | --- |
| 1. | $K_2HPO_4$ | 0.15 g |
| 2. | $MgSO_4 7H_2O$ | 0.15 g |
| 3. | Peptone | 20.00 g |
| 4. | Glycerol | 10.00 ml |
| 5. | Agar | 18.00 g |
| 6. | Distilled water | 1000 ml |
|  | Add after autoclaving |  |
| 7. | Ampicillin | 50.00 ppm |
| 8. | Chloramphenicol | 12.50 ppm |

Solid Fermentation of *P. fluorescens*:

*Pseudomonas fluorescens* obtained through the liquid fermentation has to be used for the solid fermentation using organic materials.

The composition of the substrate (organic materials) to be used in the solid fermentation Pongamia (de oiled) cake: Neem (de oiled) cake: Wheat Bran (1:1:2).

These materials have to be auto claved at 121° C. (15 PSI) for 20 min.

Inoculation of *P. fluorescens* on to Organic Materials in the Solid Fermentation:

*Pseudomonas fluorescens* obtained through the liquid fermentation has to be mixed at rate of 25 ml per kg of the above substrate filled in a tray with the lid and should be left for 10 days for the solid fermentation.

Production of the Organic Combination Formulation (Final Product) of the Bio-agents *T. harzianum* and *P. fluorescens*:

The figure is an illustrative flowchart for the production of the combination formulation of *P. fluorescens* and *T. harzianum*. The material obtained through the solid fermentation of *P. fluorescens* can be packed in one or five or ten kg pockets in aseptic conditions. Hence the organic material (Neem (de oiled) cake+Pongamia (de oiled) cake Wheat Bran) will become carrier material of the formulation or product of this bio-agent.

Characteristics of Formulation:

Neem and pongamia cakes were used as the carrier of the formulation of the product. This is also unique since this improve the establishment of the bio-control agent in the soil, it will be economical, eco-friendly and fits in the organic farming practices.

The final product will have Colony Forming Units (CFU) of *T. harzianum* to a level of $2.5 \times 10^9$/g and Colony Forming Units (CFU) of *P. fluorescens* to a level of $2.7 \times 10^9$/g.

Pathogenic contaminants

—Salmonella-not present

—Shigella—not present

—Vibrio—not present.

Other microbial contaminants are $1.6 \times 10^2$ count/gm pH is 7.2

Moisture content is 7.5%

Shelf life of the product—12 months.

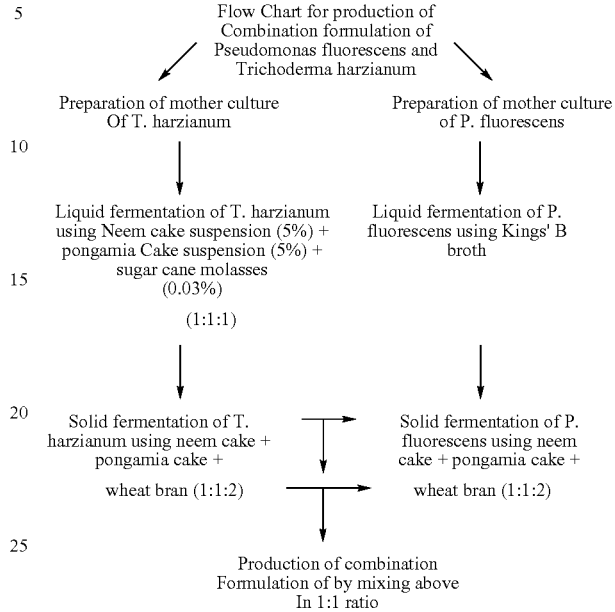

Flow Chart for production of Combination formulation of Pseudomonas fluorescens and Trichoderma harzianum The final product will have Colony Forming Units (CFU) of *T. harzianum* to a level of $2.5 \times 10^9$/g and Colony Forming Units (CFU) of *P. fluorescens* to a level of $2.7 \times 10^9$/g.

Moisture percentage—7.5%

Shelf life of the product—12 months

In the process, organic materials [neem cake (de oiled cake): pongamia cake (de oiled cake): Wheat Bran in the ratio of 1:1:2] are used as substrate in the solid fermentation of *Pseudomonas fluorescens*. This is a unique feature in this process.

After the solid fermentation of *T. harzianum* and *P. fluorescens* separately, both the bio-pesticides are mixed at in the proportion of 1-2:1-2, preferably 1:1 to get the final combination formulation of these two bio-agents. These two bio-agents are compatible and will have a shelf life of 12 months.

Organic materials [neem cake (de oiled cake)+pongamia cake (de oiled cake)+wheat Bran in the ratio of 1:1:2] act as the carrier of the formulation of final product. This is also an unique feature in this process.

It is to be noted that the formulation of the present invention is susceptible to modifications, adaptations and changes by those skilled in the art. Such variant formulations are intended to be within the scope of the present invention which is further set forth under the following claims:

We claim:

1. A process for the production of organic and combination formulation of bio-pesticide containing *Trichoderma harzianum* and *Pseudomonas fluorescens* comprising:

preparing a first mother culture, comprising a liquid fermentation of *T. harzianum* and a solid fermentation of *T. harzianum*, wherein the solid fermentation of *T. harzianum* comprises neem cake, pongamia cake and wheat bran;

preparing a second mother culture comprising liquid fermentation and solid fermentation of *P. fluorescens* separately, wherein the solid fermentation of *P. fluorescens* comprises neem cake, pongamia cake and wheat bran; and mixing said first mother culture and said second mother culture in the proportion of 1-2:1-2 to produce a final combination formulation.

2. The process of claim 1, wherein said liquid fermentation of *T. harzianum* comprises mixing 4-8% neem cake suspension, 4-8% pongamia cake suspension, and 0.02-0.05% sugarcane molasses in the ratio of 1:1:1.

3. The process of claim 1, wherein the solid fermentation of *T. harzianum* uses the neem cake, the pongamia cake and the wheat bran in 1:1:2 ratio as a substrate.

4. The process of claim 1, wherein said liquid fermentation of *P. fluorescens* is performed in kings' B broth.

5. The process of claim 1, wherein the solid fermentation of *P. fluorescens* uses the neem cake, the pongamia cake and the wheat bran in 1:1:2 ratio as a substrate.

6. The process of claim 1, wherein after solid fermentation *T. harzianum* and *P. fluorescens* are mixed in a proportion of 1-2:1-2 to produce the combination formulation.

7. The process of claim 3, wherein said solid fermentation contributes to a mass production process.

8. The process of claim 1, further comprising adding an organic material selected from the group consisting of de-oiled neem cake, de-oiled pongamia cake, wheat bran, and combinations thereof to serve as a carrier of the combination formulation.

9. The process of claim 1, wherein said first mother culture and said second mother culture are mixed in the proportion of 1:1 to produce the final combination.

10. The process of claim 1, wherein said liquid fermentation of *T. harzianum* comprises mixing 5% neem cake suspension, 5% pongamia cake suspension, and 0.03% sugarcane molasses in the ratio of 1:1:1.

11. The process of claim 6, wherein *T. harzianum* and *P. fluorescens* are mixed in the proportion of 1:1.

12. The process of claim 5, wherein said solid fermentation contributes to a mass production process.

13. The process of claim 8, wherein the organic material is de-oiled neem cake, de-oiled pongamia cake, and wheat bran in the ratio of 1:1:2.

* * * * *

UNITED STATES PATENT AND TRADEMARK OFFICE
CERTIFICATE OF CORRECTION

| | | |
|---|---|---|
| PATENT NO. | : 7,923,005 B2 | Page 1 of 1 |
| APPLICATION NO. | : 12/088039 | |
| DATED | : April 12, 2011 | |
| INVENTOR(S) | : Mahendrakar Sreenivasa Rao | |

It is certified that error appears in the above-identified patent and that said Letters Patent is hereby corrected as shown below:

Title Page; item (75);

(1) First page, Column 1, Line 2, first Inventor's address: "Hessargatta" should read -- Hessarghatta --

(2) Column 4, Line 62 and 63, Claim 1, "T harzianum" should read -- T. harzianum --

(3) Column 6, Line 1, Claim 8, "claim 1, further" should read -- claim 1 further --

Signed and Sealed this
Sixth Day of September, 2011

David J. Kappos
*Director of the United States Patent and Trademark Office*